United States Patent [19]

Meier et al.

[11] Patent Number: Plant 6,538

[45] Date of Patent: Jan. 17, 1989

[54] KENTUCKY BLUEGRASS—BA 70-139

[75] Inventors: Virgil D. Meier; Eugene W. Mayer, both of Marysville, Ohio

[73] Assignee: The O.M. Scott & Sons Company, Marysville, Ohio

[21] Appl. No.: 28,424

[22] Filed: Mar. 17, 1987

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

A variety of Kentucky bluegrass having a high level of disease resistance, excellent turf performance in the sun and shade and a high level of seed yield potential.

1 Drawing Sheet

BACKGROUND

Kentucky bluegrasses have been disclosed in U.S. Plant Pat. No. 3,156 which issued on May 9, 1972; U.S. Plant Pat. No. 3,186 which issued on May 23, 1972; U.S. Plant Pat. No., 4,336 which issued on Nov. 28, 1978; U.S. Plant patent application, Ser. No. 872,537, filed June 10, 1986; U.S. Plant patent application, Ser. No. 910,146, filed Sept. 19, 1986 and U.S. Plant patent application, Ser. No. 027,285, filed of even date herewith.

SUMMARY OF THE VARIETY

The present invention relates to a new and distinct variety of *Poa pratensis* which has been designated Ba 70-139 Kentucky bluegrass.

Ba 70-139 plant material originated by crossing a Kentucky bluegrass plant ("Gnome") disclosed in U.S. Plant patent application Ser. No. 872,537, the seed parent, with a pollen parent plant. As a result of this breeding, a distinct variety was produced and asexually propagated by rhizomes, tillers and disseminules.

Ba 70-139 Kentucky bluegrass reproduced asexually by propagules, i.e., by tillers and rhizomes and by disseminules (modified caryopses produced by apomoxis). Progeny plants have been consistently produced which are indistinguishable from the mother plant.

Ba 70-139 has a number of highly desirable characteristics including a good level of resistance to Helminthosporium spp. that causes leaf spot, melting out, and crown rot; *Ustilago striiformis* that causes stripe smut; *Erysiphe graminis* that causes powdery mildew; and Puccinia spp. that causes rust; an attractive leafy turf type growth habit; moderately wide leaf blades; an attractive green color which can be maintained throughout the entire growing season; good turf performance as evidenced by consistently high scores in tests throughout the U.S.A. and Canada, and a high seed yield potential in the bluegrass seed production region of the U.S.A.

In comparison with its seed parent, Gnome, the new variety is more shade tolerant and has better resistance to powdery mildew and rust. In comparison to the Kentucky bluegrass ("Ba 72-492") disclosed in U.S. Plant patent application, Ser. No. 027,285, filed of even date herewith and the Kentucky bluegrass ("72-500") disclosed in U.S. Plant patent application, Ser. No. 910,146, filed Sept. 19, 1986, both of which also have Gnome as their seed parent, Ba 70-139 produces seeds that are longer, has panicles that nod more, and has peduncles that are thicker than Ba 72-492; and Ba 70-139 has peduncles that are thinner and a seed yield that is higher than Ba 72-500.

DETAILED DESCRIPTION OF THE VARIETY

Figure 1:
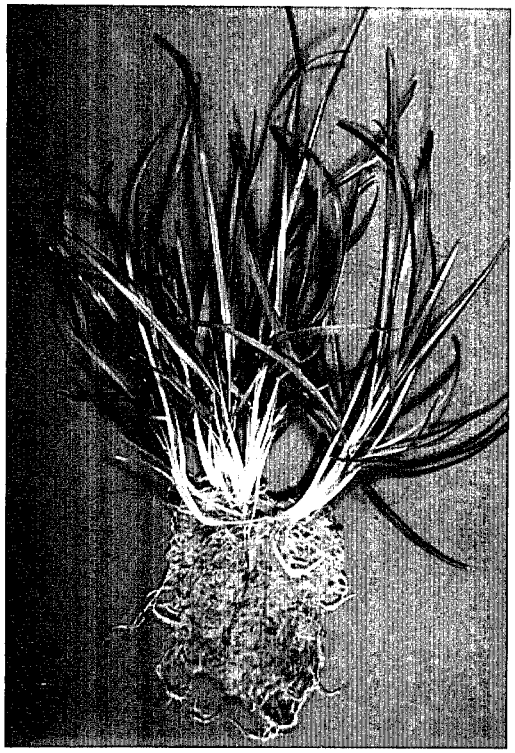
FIG. 1 is a photograph of Ba 70-139 Kentucky bluegrass plant in the vegetative stage including the extensive root and rhizome system.
Figure 2:
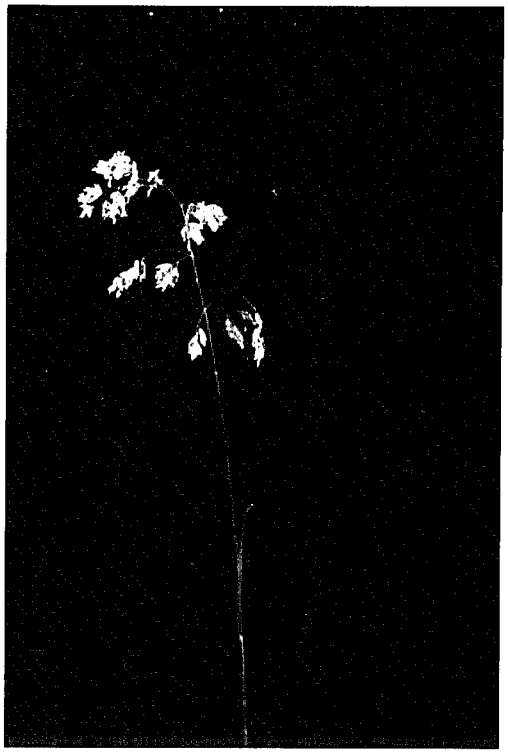
FIG. 2 is a photograph of Ba 70-139 Kentucky bluegrass panicle.
Figure 3:
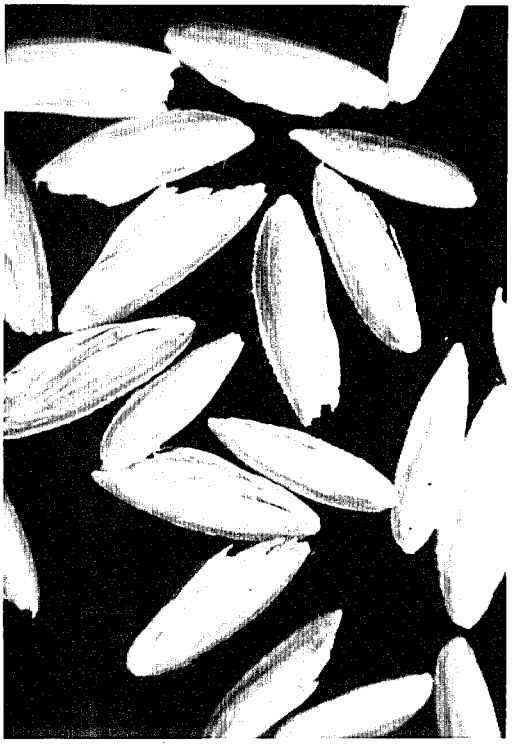
FIG. 3 is a photograph of Ba 70-139 Kentucky bluegrass seed.
Figure 4:
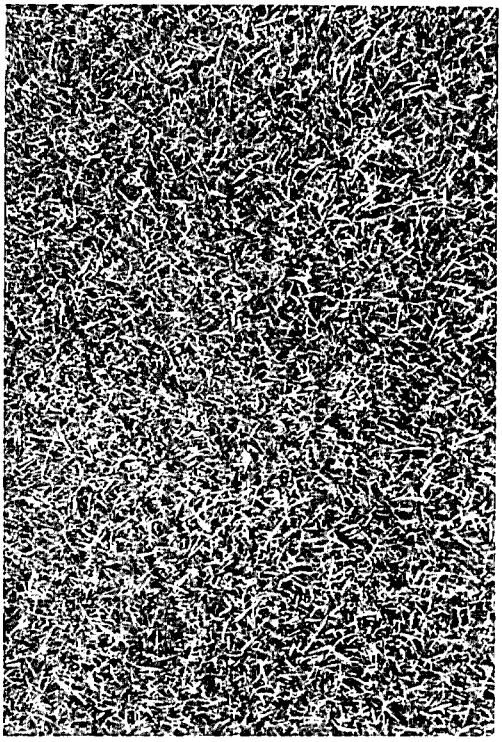
FIG. 4 is a photograph of Ba 70-139 Kentucky bluegrass turf.

Ba 70-139 Kentucky bluegrass (*Poa pratensis* L.) is perennial with creeping rhizomes forming a moderately dense turf. When plants overwinter in the field with freezing temperatures and then are brought into the greenhouse during late winter to continue growth undisturbed by clipping under moderate temperatures (60–80 degrees F.), culms are erect averaging 435 mm in length with an average of 2.7 nodes per culm. The uppermost internode averages 10.2 cm, and the peduncle averages 13.2 cm in length and 0.610 mm in thickness. The flag leaf averages 4.7 cm in length, 3.2 mm in width, and 0.112 mm in thickness. The panicle is generally nodding with an average length of 6.7 cm, width of 3.7 cm, and 4.8 whorls. The lowest whorl has an average of 3.8 branches and the third whorl from the bottom of the panicle has an average of 2.7 branches. The average spikelet at the tip of a branch in the lowest whorl is 5.2 mm in length and has 4.2 florets with an outer glume of 3.2 mm and an inner glume of 3.5 mm in length. A similar spikelet from the third whorl from the bottom of the panicle is 5.2 mm in length and has 4.0 florets with an outer glume of 3.1 mm and an inner glume of 3.5 mm in length. After the seed has been conditioned, the lemma has a generally smooth keel and almost no long, fine hairs at the base. The seed of Ba 70-139 is 2.86 mm in length and 0.78 mm in width with approximately 1,246,200 seeds per pound. Comparisons of Ba 70-139 with other bluegrasses varieties on seed measurements and on seed counts per pound are found in Tables 1 and 2.

TABLE 1

Seed Measurements of Ba 70-139 and Other Bluegrass Varieties After Conditioning.

| Variety | Length (mm) | Width (mm) |
|---|---|---|
| Ba 70-139 | 2.86 | 0.78 |
| Ba 72-492 | 2.53 | 0.76 |
| Ba 72-500 | 2.77 | 0.80 |
| Baron | 3.07 | 0.86 |
| Bristol | 2.73 | 0.80 |
| Nassau | 2.96 | 0.78 |
| Newport | 2.76 | 0.71 |
| Park | 3.04 | 0.72 |
| Ram I | 3.51 | 0.84 |
| Victa | 3.20 | 0.86 |
| LSD(.05) | 0.19 | 0.06 |

TABLE 2

Comparison of Seed Counts Per Pound of Ba 70-139 and Other Bluegrass Varieties After Conditioning.

| | |
|---|---|
| Ba 70-139 | 1,246,200 |
| Adelphi | 1,383,976 |
| America | 1,659,824 |
| Gnome | 1,017,641 |
| Baron | 1,051,693 |
| Birka | 1,223,530 |
| Bonnieblue | 1,135,303 |
| Bristol | 1,270,821 |
| Eclipse | 1,335,668 |
| Glade | 1,108,441 |
| Kenblue | 1,463,923 |
| Merit | 1,109,728 |
| Nassau | 1,127,130 |
| Newport | 1,226,481 |
| Park | 1,248,349 |
| Sydsport | 1,355,644 |
| Vantage | 1,555,303 |
| Victa | 1,038,298 |

Since environmental conditions such as soil and climate may influence morphological characters to some extent, comparisons of morphological characteristics of Ba 70-139 are made with other Kentucky bluegrass varieties in Table 3-10.

TABLE 3

Morphological Comparison of Panicles of Ba 70-139 and Other Bluegrass Varieties in the Greenhouse at Marysville, Ohio

| Variety | Panicle Nodding* | Panicle Length (cm) | Panicle Width (cm) | Number of Whorls Per Panicle | Number of Branches Lower Whorl | Number of Branches Third Whorl |
|---|---|---|---|---|---|---|
| Ba 70-139 | 2.0 | 6.7 | 3.7 | 4.8 | 3.8 | 2.7 |
| Ba 72-492 | 1.2 | 7.5 | 4.2 | 5.5 | 4.0 | 3.0 |
| Ba 72-500 | 2.0 | 6.8 | 3.8 | 5.0 | 4.0 | 2.4 |
| Baron | 1.0 | 7.8 | 4.1 | 5.2 | 3.8 | 2.5 |
| Bristol | 2.0 | 9.7 | 5.0 | 5.0 | 3.3 | 2.7 |
| Nassau | 2.0 | 10.0 | 6.0 | 5.0 | 3.0 | 2.0 |
| Newport | 2.0 | 10.3 | 4.4 | 4.5 | 2.3 | 2.3 |
| Park | 1.6 | 9.0 | 3.7 | 4.0 | 4.3 | 3.7 |
| Ram I | 2.0 | 9.0 | 4.7 | 4.0 | 2.5 | 2.0 |
| Victa | 1.2 | 7.5 | 4.1 | 5.4 | 4.4 | 3.4 |
| LSD (.05) | 0.5 | 1.6 | 1.0 | 0.8 | 0.7 | 0.8 |

*Panicle nodding rated 1 = erect, 2 = nodding.

TABLE 4

Morphological Comparison of Spikelets of Ba 70-139 and Other Bluegrass Varieties in the Greenhouse at Marysville, Ohio.

| Variety | Spikelet Length (mm) Lowest Whorl | Spikelet Length (mm) Third Whorl | Number of Florets per Spikelet Lowest Whorl | Number of Florets per Spikelet Third Whorl |
|---|---|---|---|---|
| Ba 70-139 | 5.2 | 5.2 | 4.2 | 4.0 |
| Ba 72-492 | 5.2 | 5.0 | 4.4 | 4.2 |
| Ba 72-500 | 5.1 | 5.0 | 4.2 | 3.9 |
| Baron | 5.0 | 5.0 | 3.7 | 3.8 |
| Bristol | 6.2 | 6.0 | 5.7 | 5.3 |
| Nassau | 4.6 | 4.6 | 4.5 | 4.5 |
| Newport | 5.3 | 5.2 | 5.2 | 5.2 |
| Park | 6.5 | 6.7 | 5.2 | 4.7 |
| Ram I | 4.7 | 5.2 | 5.2 | 5.5 |
| Victa | 5.2 | 5.0 | 3.8 | 3.8 |
| LSD(.05) | 0.9 | 0.8 | 1.1 | 1.0 |

TABLE 5

Morphological Comparison of Glumes of Ba 70-139 and Other Bluegrass Varieties in the Greenhouse at Marysville, Ohio.

| Variety | Glume Length (mm) Outer Lowest Whorl | Glume Length (mm) Outer Third Whorl | Glume Length (mm) Inner Lowet Whorl | Glume Length (mm) Inner Third Whorl |
|---|---|---|---|---|
| Ba 70-139 | 3.2 | 3.1 | 3.5 | 3.5 |
| Ba 72-492 | 2.9 | 3.0 | 3.3 | 3.3 |
| Ba 72-500 | 3.1 | 3.1 | 3.4 | 3.4 |
| Baron | 2.9 | 2.8 | 3.4 | 3.3 |
| Bristol | 3.4 | 3.3 | 3.7 | 3.9 |
| Nassau | 2.3 | 2.4 | 2.7 | 2.7 |
| Newport | 2.6 | 2.5 | 2.9 | 2.9 |
| Park | 3.0 | 3.2 | 3.5 | 3.7 |
| Ram I | 2.6 | 2.4 | 2.9 | 2.7 |
| Victa | 2.8 | 3.0 | 3.3 | 3.3 |
| LSD(.05) | 0.5 | 0.4 | 0.4 | 0.4 |

TABLE 6

Morphological Comparison of Flag Leaves of Ba 70-139 and Other Bluegrass Varieties in the Greenhouse at Marysville, Ohio.

| Variety | Flag Leaf Length (cm) | Flag Leaf Width (mm) | Flag Leaf Thickness (mm) |
|---|---|---|---|
| Ba 70-139 | 4.7 | 3.2 | 0.112 |
| Ba 72-492 | 5.2 | 3.6 | 0.117 |
| Ba 72-500 | 4.1 | 3.2 | 0.112 |
| Baron | 4.5 | 3.2 | 0.119 |
| Bristol | 5.5 | 3.4 | 0.127 |
| Nassau | 6.1 | 3.1 | 0.127 |
| Newport | 6.2 | 3.5 | 0.135 |
| Park | 4.2 | 2.6 | 0.109 |
| Ram I | 4.7 | 3.1 | 0.127 |
| Victa | 5.9 | 4.0 | 0.124 |
| LSD(.05) | 1.8 | 0.6 | 0.013 |

TABLE 7

Morphological Comparison of Peduncles, Culms, and Internodes of Ba 70-139 and Other Bluegrass Varieties in the Greenhouse at Marysville, Ohio.

| Variety | Peduncle Length (cm) | Peduncle Width (mm) | Culm Length (mm) | Number of Nodes Per Culm | Top Internode Length (cm) |
|---|---|---|---|---|---|
| Ba 70-139 | 13.2 | 0.610 | 435 | 2.7 | 10.2 |
| Ba 72-492 | 12.6 | 0.558 | 486 | 2.2 | 10.5 |
| Ba 72-500 | 12.9 | 0.660 | 439 | 2.7 | 9.8 |
| Baron | 12.7 | 0.559 | 482 | 2.5 | 10.1 |
| Bristol | 15.0 | 0.686 | 522 | 2.7 | 11.3 |
| Nassau | 8.0 | 0.533 | 450 | 2.5 | 11.2 |

TABLE 7-continued

Morphological Comparison of Peduncles, Culms, and Internodes of Ba 70-139 and Other Bluegrass Varieties in the Greenhouse at Marysville, Ohio.

| Variety | Peduncle Length (cm) | Peduncle Width (mm) | Culm Length (mm) | Number of Nodes Per Culm | Top Internode Length (cm) |
|---|---|---|---|---|---|
| Newport | 18.0 | 0.558 | 547 | 2.3 | 11.2 |
| Park | 14.3 | 0.787 | 578 | 3.0 | 13.0 |
| Ram I | 18.5 | 0.610 | 527 | 3.0 | 10.2 |
| Victa | 12.2 | 0.711 | 474 | 2.4 | 10.6 |
| LSD(.05) | 3.7 | 0.018 | 79 | 0.6 | 2.1 |

TABLE 8

Morphological Comparison of Leaves of Ba 70-139 and Other Bluegrass Varieties in the Greenhouse at Marysville, Ohio.

| Variety | Ligule Length (mm) | Leaf Length (mm) | Leaf Width (mm) | Leaf Angle (Degrees From Horizontal) |
|---|---|---|---|---|
| Ba 70-139 | 0.26 | 218 | 4.1 | 55 |
| Ba 72-492 | 0.28 | 239 | 4.4 | 52 |
| Ba 72-500 | 0.25 | 204 | 4.1 | 50 |
| Baron | 0.30 | 313 | 4.4 | 63 |
| Bristol | 0.30 | 253 | 4.3 | 37 |
| Nassau | 0.22 | 226 | 3.5 | 39 |
| Newport | 0.22 | 251 | 4.1 | 50 |
| Park | 0.33 | 329 | 4.2 | 44 |
| Ram I | 0.18 | 188 | 3.7 | 40 |
| Victa | 0.28 | 235 | 4.3 | 52 |
| LSD(.05) | 0.11 | 49 | 0.6 | 10 |

TABLE 9

Morphological Comparison of Leaf Hairs of Ba 70-139 and Other Bluegrass Varieties in the Greenhouse at Marysville, Ohio.

| Variety | Hairs[a] Around Ligule on Upper Surface of the Leaf | Hairs[a] on Collar | Hairs[b] on Ligule |
|---|---|---|---|
| Ba 70-139 | 1.0 | 3.5 | 1.5 |
| Ba 72-492 | 1.0 | 3.2 | 1.3 |
| Ba 72-500 | 1.0 | 3.5 | 2.7 |
| Baron | 1.0 | 5.0 | 4.0 |
| Bristol | 1.3 | 4.7 | 4.3 |
| Nassau | 2.7 | 5.0 | 1.0 |
| Newport | 1.0 | 4.0 | 0.8 |
| Park | 1.0 | 1.7 | 0.0 |
| Ram I | 1.0 | 3.7 | 0.3 |
| Victa | 1.0 | 3.3 | 2.2 |
| LSD(.05) | 0.3 | 1.4 | 1.8 |

[a]hairs around ligule and on collar rated 1–5: 1 = none, 5 = many
[b]Hairs on ligule rated 0–5: 0 = none, 5 = many

TABLE 10

Morphological Comparisons of Ba 70-139 and Other Bluegrass Varieties Grown as Unmowed Spaced Plants in the Field at Marysville, Ohio.

| | Mature Plant Height | Panicle Density | Seedhead Weight |
|---|---|---|---|
| Ba 70-139 | 35 | 5 | 402 |
| Adelphi | 42 | 3 | 345 |
| Nugget | 17 | 3 | 233 |
| Bristol | 40 | 4 | 511 |
| Merion | 25 | 2 | 320 |
| Glade | 20 | 3 | 214 |
| Vantage | 52 | 2 | 1019 |
| Victa | 23 | 2 | 648 |

Ratings: Mature Plant Height (cm) includes panicle Panicle Density - 1–10, 10 = high panicle density Seedhead Weight - Weight (mg) of 3 panicles Ba 70-139 has performed well throughout the U.S.A. and Canada, as exhibited by high turf quality ratings in many different locations in comparison to other varieties. In addition, Ba 70-139 tolerates shady growing conditions very well, which is an important characteristic that allows an even broader range of use. The new variety has a pleasant medium green color which can be maintained throughout the growing season and widely scattered locations in the U.S.A. and Canada. The color of Ba 70-139 is enhanced compared to other varieties when grown in the shade due to its high tolerance to the various stresses and diseases that occur frequently under shady conditions. Comparisons of Ba 70-139 with other varieties for quality, color, and shade performance are shown in Tables 11–14.

TABLE 11

Comparison of the Turf Quality of BA 70-139 and Other Bluegrass Varieties in the U.S.A.

| Variety | St. Louis Missouri 1 Year Mean | Adelphia New Jersey 2 Year Mean | Marysville Ohio 5 Year Mean |
|---|---|---|---|
| BA 70-139 | 3.2 | 6.1 | 2.3 |
| America | 2.8 | | |
| Adelphi | 2.9 | 6.4 | 2.3 |
| Banff | | | |
| Baron | 2.7 | 6.4 | 2.3 |
| Birka | 2.3 | 5.9 | |
| Bonnieblue | | 6.7 | |
| Bristol | 2.7 | 6.5 | |
| Columbia | | 5.9 | |
| Eclipse | | 7.2 | |
| Flyking | | 5.7 | |
| Glade | 2.8 | 6.7 | 2.3 |
| Gnome | 2.9 | 6.4 | 2.2 |
| Kenblue | | 3.3 | |
| Merion | | 6.0 | 2.1 |
| Merit | 2.8 | 6.2 | |
| Midnight | | 7.3 | |
| Monopoly | | 5.7 | |
| Nassau | | 5.9 | |
| Newport | | | 2.0 |
| Nugget | | | 2.4 |
| Parade | | 5.6 | |
| Park | 1.8 | | |
| Ram I | | 6.2 | |
| Sydsport | 2.7 | 6.0 | |
| Touchdown | 2.7 | 6.1 | |
| Vantage | 2.6 | 3.6 | 2.1 |
| Victa | 2.8 | 6.5 | 2.3 |
| Wabash | | 4.8 | |
| Windsor | | | 2.0 |

| | | Maryland | |
|---|---|---|---|
| Variety | Gervais Oregon 1 Year Mean | Beltsville 1 Year Mean | Prince Frederick 1 Year Mean |
| Ba 70-139 | 2.9 | 5.8 | 2.4 |
| America | | | |
| Adelphi | 2.8 | 5.9 | 2.0 |
| Banff | | 4.8 | |
| Baron | | 5.3 | |
| Birka | | | |
| Boonieblue | | 5.0 | 1.1 |
| Bristol | 3.0 | 5.0 | 1.5 |
| Columbia | | 4.9 | |
| Eclipse | | 5.9 | |
| Flyking | | 4.9 | |
| Glade | | 5.3 | 1.3 |
| Gnome | | | |
| Kenblue | | | |
| Merion | | 5.3 | 1.2 |
| Merit | | 6.1 | 1.5 |
| Midnight | | 5.5 | |
| Monopoly | | 4.9 | |
| Nassau | | 4.5 | |
| Newport | | | |
| Nugget | | | |
| Parade | | 5.0 | |

TABLE 11-continued

Comparison of the Turf Quality of BA 70-139 and Other Bluegrass Varieties in the U.S.A.

| | | | |
|---|---|---|---|
| Park | 1.8 | | 1.3 |
| Ram I | 2.4 | 4.6 | |
| Sydsport | | 5.8 | |
| Touchdown | | 5.8 | |
| Vantage | | 5.5 | 2.0 |
| Victa | 2.7 | 5.5 | 1.6 |
| Wabash | | | |
| Windsor | | | |

Rating Scale: Larger number indicates higher quality.

TABLE 12

Comparison of Turf Color of Ba 70-139 and Other Bluegrass Varieties at Various Locations in the U.S.A.

| Variety | St. Louis Missouri 1 Year Mean | Somis California 1 Year Mean | Gervais Oregon 2 Year Mean | Prince Frederick Maryland 1 Year Mean | Marysville Ohio 3 Year Mean |
|---|---|---|---|---|---|
| Ba 70-139 | 9.1 | 6.3 | 8.7 | 6.9 | 8.5 |
| Adelphi | 9.4 | 6.5 | 9.6 | 6.7 | 8.7 |
| America | 9.4 | | | | |
| Baron | 9.2 | | | | |
| Birka | 9.1 | 6.3 | | | |
| Bono | 9.0 | 6.2 | | | |
| Bristol | 9.5 | 7.6 | 9.5 | 7.3 | |
| Fylking | | | | | 8.4 |
| Glade | 9.3 | 7.0 | | 7.4 | 8.8 |
| Gnome | 9.3 | | | | 8.7 |
| Kenblue | | 5.8 | | | |
| Merion | | | | 4.7 | 8.4 |
| Merit | | 5.8 | | | |
| Midnight | | 5.5 | | | |
| Newport | | 6.0 | | | 8.3 |
| Nugget | | | | | 8.8 |
| Park | 9.0 | | 6.9 | 5.5 | |
| Ram I | | 7.3 | 8.6 | | |
| Rugby | | 6.7 | | | |
| Sydsport | 9.2 | | | | |
| Touchdown | 9.0 | | | | |
| Vantage | 9.2 | 5.7 | | 6.3 | 8.4 |
| Victa | 9.2 | 6.0 | 8.5 | 6.8 | 8.7 |
| Windsor | | | | | 8.4 |
| LSD(.05) | 0.3 | | | | 0.2 |

Rating Scale: Larger number indicates darker green color.

TABLE 13

Turf Performance Ratings Under Natural Shade of Ba 70-139 and Other Bluegrass Varieties.

| | Prince Frederick | Marysville Ohio | | | |
|---|---|---|---|---|---|
| Variety | Maryland 3 Year Mean | Test 1 4 Year Mean | Test 2 4 Year Mean | Test 3 4 Year Mean | Test 4 2 Year Mean |
| Ba 70-139 | 2.1 | 2.6 | 2.4 | 3.1 | 2.6 |
| Adelphi | | | | 2.6 | 2.0 |
| Banff | | 2.4 | | | |
| Birka | | | | 2.2 | |
| Bonniblue | | | 1.9 | 1.9 | |
| Bristol | 1.8 | 2.4 | 2.0 | 2.6 | 1.7 |
| Flyking | | | 1.9 | 1.5 | |
| Glade | | 2.1 | | 2.5 | 1.5 |
| Merion | | | 1.8 | 2.2 | 1.7 |
| Monopoly | | 2.8 | | | 2.4 |
| Nassau | | | | | 1.9 |
| Newport | 1.2 | 1.8 | 1.9 | | |
| Nugget | | | | 2.3 | |
| Parade | | | 2.0 | 2.3 | |
| Park | | | 1.9 | | 1.8 |
| Ram I | | | | | 2.0 |
| Rugby | | 2.2 | | | |
| Sydsport | | | | 2.5 | |
| Touchdown | | | 1.9 | 2.1 | |
| Vantage | | | | 1.8 | 2.2 |

TABLE 13-continued

Turf Performance Ratings Under Natural Shade of Ba 70-139 and Other Bluegrass Varieties.

| | Prince Frederick | Marysville Ohio | | | |
|---|---|---|---|---|---|
| Variety | Maryland 3 Year Mean | Test 1 4 Year Mean | Test 2 4 Year Mean | Test 3 4 Year Mean | Test 4 2 Year Mean |
| Victa | 1.2 | 1.7 | 1.8 | 2.0 | 1.5 |
| Wabash | | | | | 2.2 |
| Windsor | | | | 1.7 | |

Rated 1–4, 4 = Best

TABLE 14

Comparison of Turf Color Under Natural Shade Conditions of Ba 70-139 and Other Bluegrass Varieties.

| | Marysville Ohio | | | | Prince Frederick Maryland 3 Year |
|---|---|---|---|---|---|
| | Test 1 | Test 2 | Test 3 | Test 4 | Mean |
| Ba 70-139 | 8.8 | 8.3 | 8.3 | 8.2 | 8.2 |
| Adelphi | | | 7.8 | 7.9 | |
| America | | | 7.5 | | |
| Banff | | 8.3 | | | |
| Bonnieblue | 8.5 | | 7.5 | | |
| Bristol | 8.4 | 7.8 | 7.5 | 7.9 | 8.2 |
| Flyking | 8.1 | | | | |
| Glade | | 8.0 | 7.5 | 8.1 | |
| Merion | 8.3 | | | 8.1 | |
| Monopoly | | 8.3 | | 7.8 | |
| Mystic | | | 7.8 | | |
| Nassau | | | | 8.0 | |
| Newport | 8.3 | 7.5 | 8.2 | | 5.5 |
| Nugget | 8.3 | | | | |
| Parade | 8.2 | | | | |
| Park | 8.1 | | 7.0 | 7.8 | |
| Ram I | | | 7.8 | 8.0 | |
| Rugby | | 8.3 | | | |
| Sydsport | | | 7.5 | | |
| Touchdown | 8.3 | | | | |
| Vantage | | | | 8.0 | |
| Victa | 8.3 | 8.0 | 7.9 | 8.1 | 6.0 |
| Wabash | | 7.5 | | 8.0 | |
| LSD(.05) | | 0.4 | 0.7 | 0.3 | |

Rated 1–9, 9 = darkest green

Turf diseases are one of the major causes of inconsistent and poor turf performance among locations and years. Comparisons of resistance to leaf spot (also known as melting out and crown rot) caused by *Helminthosporium vagans,* powdery mildew caused by *Erysiphe graminis,* rust caused by Puccinia spp., dollarspot caused by *Sclerotina homeocarpa,* and stripe smut caused by *Ustilago striiformis,* are presented in Tables 15–21.

TABLE 15

Comparison of Leafspot Disease Incidence on Ba 70-139 and Other Bluegrasses at Several Locations in the U.S.A.

| Variety | St. Louis[a] Missouri | Beltsville[b] Maryland | Adelphia[b] New Jersey |
|---|---|---|---|
| Ba 70-139 | 2 | 7.3 | 7.0 |
| A-34 | | 5.3 | 4.3 |
| Adelphi | 2 | 8.0 | 5.7 |
| America | 8 | | |
| Banff | | 5.3 | 7.0 |
| Baron | 2 | 7.0 | 8.7 |
| Birka | 5 | | 6.3 |
| Bonnieblue | | | 7.0 |
| Bono | 7 | | |
| Bristol | 2 | 7.0 | 8.3 |
| Columbia | | 5.7 | 6.3 |
| Eclipse | | 7.7 | 9.0 |
| Flyking | | 6.7 | 6.3 |
| Glade | 2 | 7.3 | 6.3 |

TABLE 15-continued

Comparison of Leafspot Disease Incidence on Ba 70-139 and Other Bluegrasses at Several Locations in the U.S.A.

| | | | |
|---|---|---|---|
| Gnome | 2 | 7.0 | 8.0 |
| Kenblue | | 3.3 | 1.7 |
| Merion | | 6.3 | 7.7 |
| Merit | 3 | 7.3 | 7.7 |
| Midnight | | 7.0 | 7.0 |
| Monopoly | | 5.3 | 6.0 |
| Mystic | | | |
| Nassau | | 7.7 | 7.4 |
| Parade | | 6.0 | 5.0 |
| Park | 52 | | |
| Ram I | | 6.5 | 7.0 |
| Rugby | | | 5.0 |
| Sydsport | 3 | 7.3 | 6.3 |
| Touchdown | 7 | 7.7 | |
| Vantage | 7 | 5.0 | 2.0 |
| Victa | 2 | 8.0 | 7.0 |
| Wabash | | | 2.0 |
| Windsor | | | |
| LSD(.05) | 7 | | 1.9 |

| Variety | Gervais[a] Oregon | Accokeek[a] Maryland | Marysville[a] Ohio |
|---|---|---|---|
| Ba 70-139 | 7 | 4 | 0 |
| A-34 | | | |
| Adelphi | 0 | | |
| America | | | |
| Banff | | | |
| Baron | | | |
| Birka | | | |
| Boonieblue | | | |
| Bono | | | |
| Bristol | 1 | 3 | 0 |
| Columbia | | | |
| Eclipse | | | |
| Flyking | | 16 | |
| Glade | | | 27 |
| Gnome | | | 0 |
| Kenblue | | 3 | 40 |
| Merion | | 5 | 0 |
| Merit | | | |
| Midnight | | | |
| Monopoly | | | 13 |
| Mystic | | | 35 |
| Nassau | | | |
| Parade | | | |
| Park | 13 | | 40 |
| Ram I | 3 | | |
| Rugby | | | |
| Sydsport | | | 0 |
| Touchdown | | | |
| Vantage | | 5 | |
| Victa | 3 | | 0 |
| Wabash | | | |
| Windsor | | 53 | |
| LSD(.05) | 5 | 22 | 9 |

Ratings
[a]% of turf affected by disease
[b]1–9, 9= least disease

TABLE 16

Comparison of Powdery Mildew Disease Incidence Under Natural Shade Conditions on Ba 70-139 and Other Bluegrasses.

| Variety | Prince Frederick Maryland | Marysville Ohio Test 1 | Test 2 | Test 3 | Test 4 |
|---|---|---|---|---|---|
| Ba 70-139 | 5 | 5 | 0 | 15 | 0 |
| Adelphi | | 15 | | | 10 |
| America | | | 13 | | 0 |
| Banff | | | | 45 | |
| Baron | | | | | |
| Birka | | 8 | 3 | | |
| Bonnieblue | | 58 | | | 0 |
| Bristol | 5 | 5 | 2 | 30 | 10 |
| Columbia | | | | | |
| Eclipse | | | 5 | | |
| Flyking | | 50 | | | |

TABLE 16-continued

Comparison of Powdery Mildew Disease Incidence Under Natural Shade Conditions on Ba 70-139 and Other Bluegrasses.

| Variety | Prince Frederick Maryland | Marysville Ohio Test 1 | Test 2 | Test 3 | Test 4 |
|---|---|---|---|---|---|
| Glade | | 5 | 36 | 65 | 0 |
| Gnome | | | 72 | | |
| Kenblue | | | 4 | | |
| Merion | | 83 | | | |
| Merit | | | | | |
| Midnight | | | | | |
| Monopoly | | | | 5 | |
| Mystic | | | | | 5 |
| Nassau | | | | | |
| Newport | 53 | | | 75 | 0 |
| Nugget | | 18 | | | |
| Parade | | 60 | | | |
| Park | | | | | 0 |
| Ram I | | | | | 25 |
| Rugby | | | | 40 | |
| Sydsport | | 15 | | | 20 |
| Touchdown | | 5 | 0 | | |
| Vantage | | 30 | | | |
| Victa | 60 | 84 | 69 | 60 | 8 |
| Windsor | | 26 | | | |
| LSD(.05) | 10 | 22 | | 31 | 8 |

Rated as % of turf affected by disease.

TABLE 17

Comparison of Powdery Mildew Disease Incidence Under Conditions Other Than Natural Shade on Ba 70-139 and Other Bluegrasses.

| Variety | Greenhouse New Brunswick[a] New Jersey | Greenhouse Marysville[b] Ohio | Spaced Plants - Sun[c] Marysville Ohio |
|---|---|---|---|
| Ba 70-139 | 4.7 | 2 | 0 |
| Adelphi | 0.8 | 6 | |
| America | 6.7 | | |
| Banff | 0.4 | | |
| Baron | 1.4 | 9 | 2 |
| Birka | 5.7 | | |
| Bonnieblue | 0.8 | | |
| Bristol | 6.4 | 2 | 2 |
| Columbia | 0.5 | | |
| Eclipse | 6.9 | | |
| Flyking | 1.3 | | |
| Glade | 7.0 | 7 | |
| Gnome | 1.7 | | |
| Kenblue | | | 2 |
| Merion | 0.9 | 6 | 1 |
| Merit | 2.3 | 8 | |
| Midnight | 0.7 | | |
| Monopoly | 5.9 | | |
| Mystic | 8.3 | | |
| Nassau | | 7 | |
| Newport | | 2 | |
| Nugget | 7.0 | | 0 |
| Parade | 2.2 | | |
| Park | | 6 | 2 |
| Ram I | 7.2 | 2 | |
| Rugby | 0.6 | | |
| Sydsport | 6.1 | 2 | |
| Touchdown | | | |
| Vantage | 5.0 | 4 | |
| Victa | 1.9 | 9 | 3 |
| Windsor | | | 3 |
| LSD(.05) | 0.8 | 3 | 2 |

[a]Rated 0–9, 9 = least disease
[b]Rated 1–9, 9 = most disease
[c]Rated 1–5, 5 = most disease

TABLE 18

Comparison of Rust (Puccinia spp.) Disease Incidence on Ba 70-139 and Other Bluegrasses.

| | Turf[b] Gervais Oregon | | Unmowed Spaced Plants[a] Marysville Ohio | |
|---|---|---|---|---|
| Variety | Test 1 | Test 2 | Test 1 | Test 2 |
| Ba 70-139 | 12 | 1 | 1 | 0 |
| Adelphi | | 4 | | 0 |
| Baron | | | 3 | |
| Bristol | 7 | 2 | 2 | 0 |
| Glade | | | | 0 |
| Kenblue | | | 2 | |
| Merion | | | 2 | 2 |
| Nugget | | | 3 | 0 |
| Park | | 49 | 1 | |
| Ram I | | 15 | | |
| Victa | 63 | 13 | 2 | 1 |
| Vantage | | | | 2 |
| Windsor | | | 3 | |
| LSD(.05) | 26 | | 1 | |

[a]Rated 1-5, 5 = most disease
[b]Rated as % of disease incidence

TABLE 19

Comparison of Stem Rust (*Puccinia graminis*) Disease Incidence on Ba 70-139 and Other Bluegrasses at Adelphia, New Jersey.

| | Test 1 | Test 2 |
|---|---|---|
| Ba 70-139 | 7.8 | 7.2 |
| Midnight | 7.0 | 7.8 |
| Columbia | 6.7 | 7.8 |
| Banff | 6.5 | 7.7 |
| Bristol | 7.7 | 7.7 |
| Parade | 6.2 | 7.5 |
| Monopoly | 7.1 | 7.4 |
| Ram I | 7.0 | 7.3 |
| Victa | 5.6 | 7.2 |
| Merit | 5.7 | 7.0 |
| Baron | 6.4 | 7.0 |
| Nassau | 6.8 | 7.0 |
| Eclipse | 4.7 | 7.0 |
| Bonnieblue | 5.4 | 7.0 |
| Adelphi | 7.1 | 6.9 |
| America | 7.4 | 6.9 |
| Vantage | 6.2 | 5.9 |
| Touchdown | 3.5 | 5.7 |
| Birka | 3.5 | 5.6 |
| Merion | 2.4 | 3.6 |
| LSD(.05) | 0.9 | 1.0 |

Rated 1-9, 9 = No Disease

TABLE 20

Comparison of Dollarspot Disease Incidence on Ba 70-139 and Other Bluegrasses.

| | Prince Frederick | Marysville Ohio | |
|---|---|---|---|
| Variety | Maryland | Test 1 | Test 2 |
| Ba 70-139 | 30 | 37 | 32 |
| Adelphi | 8 | 20 | 36 |
| America | | 13 | |
| Banff | | | 70 |
| Baron | 50 | 23 | 53 |
| Birka | 6 | 47 | |
| Bonnieblue | 10 | | 57 |
| Bono | 4 | 63 | |
| Bristol | 6 | 17 | 43 |
| Columbia | 10 | | |
| Eclipse | | 8 | 60 |
| Glade | | 40 | 43 |
| Gnome | | 22 | |
| Kenblue | 8 | 37 | 30 |
| Merion | | | 50 |
| Merit | 4 | | 50 |
| Midnight | 6 | | |
| Newport | | | 67 |
| Park | | 33 | 43 |

TABLE 20-continued

Comparison of Dollarspot Disease Incidence on Ba 70-139 and Other Bluegrasses.

| | Prince Frederick | Marysville Ohio | |
|---|---|---|---|
| Variety | Maryland | Test 1 | Test 2 |
| Ram I | 40 | | 25 |
| Rugby | 12 | | 73 |
| Sydsport | | 43 | |
| Touchdown | | 50 | |
| Vantage | 11 | 15 | 32 |
| Victa | 5 | 23 | 30 |
| Wabash | 11 | | |
| Windsor | | | 33 |
| LSD(.05) | 19 | 24 | 38 |

Rating: % of turf that is affected by disease.

TABLE 21

Comparison of Stripe Smut Disease Incidence on Ba 70-139 and Other Bluegrasses in Maryland.

| Variety | Prince Frederick | Accokeek |
|---|---|---|
| Ba 70-139 | 0 | 0 |
| Bristol | 13 | 0 |
| Flyking | | 2 |
| Kenblue | | 0 |
| Merion | | 2 |
| Mosa | 28 | |
| Vantage | | 4 |
| Windsor | | 58 |
| LSD(.05) | 18 | 8 |

Rating: % of turf that is affected by disease.

Ba 70-139 has the capability to tolerate heat and drought stress, and it has a low growth habit and a lower vertical growth rate than many varieties, especially the common type of varieties such as Park, Kenblue, and Newport, that should allow it to tolerate lower mowing heights and possibly decrease the total number of mowings per year without sacrificing overall turf performance. The leaf texture of the new variety is similar to many bluegrass varieties when maintained under mowed turf conditions. Comparisons showing heat and drought stress, low growth habit, and leaf texture are presented in Tables 22-24.

TABLE 22

Comparison of Drought and Heat Tolerance of Ba 70-139 and Other Bluegrass in Maryland.

| Variety | Test 1 | Test 2 | Test 3 | Test 4 |
|---|---|---|---|---|
| Ba 70-139 | 6 | 0 | 8 | 3 |
| Adelphi | | | 7 | 4 |
| Baron | | | | 0 |
| Birka | | | | 11 |
| Bonnieblue | | | 12 | 8 |
| Bono | | | | 10 |
| Bristol | 31 | 50 | 10 | 5 |
| Flyking | | 50 | | |
| Glade | | | 13 | |
| Kenblue | | 50 | | 7 |
| Merion | | 25 | 20 | |
| Merit | | | 18 | 2 |
| Midnight | | | | 17 |
| Mosa | 27 | | | |
| Park | | | 20 | 3 |
| Ram I | | | | 0 |
| Rugby | | | | 6 |
| Vantage | | 0 | 7 | 7 |
| Victa | | | 17 | 10 |
| Wabash | | | | 13 |
| Windsor | | 50 | | |
| LSD(.05) | | 33 | 14 | |

Rated as % brown turf due to drought and heat stress.

TABLE 23

Comparison of Growth habit of Ba 70-139 and Other Bluegrasses at Marysville, Ohio.

| Variety | Test 1 | Test 2 |
|---|---|---|
| Ba 70-139 | 2.0 | 1.8 |
| Adelphi | 2.0 | 2.1 |
| America | 1.8 | |
| Baron | 1.8 | 2.0 |
| Birka | 2.0 | |
| Bono | 2.0 | |
| Bristol | 2.0 | |
| Eclipse | 2.0 | |
| Flyking | | 2.3 |
| Glade | 2.2 | 1.7 |
| Gnome | 2.0 | 1.7 |
| Kenblue | 2.9 | |
| Merion | | 2.2 |
| Newport | | 2.4 |
| Nugget | | 1.5 |
| Park | 2.9 | |
| Sydsport | 1.9 | |
| Touchdown | 2.0 | |
| Vantage | 2.7 | 3.0 |
| Victa | 1.9 | 1.8 |
| Windsor | | 2.0 |
| LSD(.05) | 0.3 | |

Rated 1–5, 5 = Highest Growth Habit

TABLE 24

Comparison of Leaf Texture of Ba 70-139 and Other Bluegrasses Under Mowed Turf Conditions.

| Variety | St. Louis Missouri | Gervais Oregon |
|---|---|---|
| Ba 70-139 | 4.0 | 2.0 |
| Adelphi | 5.3 | 2.8 |
| America | 6.0 | |
| Baron | 4.6 | |
| Birka | 6.0 | |
| Bono | 5.6 | |
| Bristol | 5.3 | 3.0 |
| Glade | 6.0 | |
| Gnome | 4.3 | |
| Merit | 4.3 | |
| Park | 6.0 | 3.0 |
| Ram I | | 3.0 |
| Sydsport | 5.0 | |
| Touchdown | 5.0 | |
| Vantage | 6.0 | |
| Victa | 4.4 | 1.7 |

TABLE 24-continued

Comparison of Leaf Texture of Ba 70-139 and Other Bluegrasses Under Mowed Turf Conditions.

| Variety | St. Louis Missouri | Gervais Oregon |
|---|---|---|
| LSD(.05) | 0.7 | 0.5 |

Rating: Largest number indicates finest texture

Ba 70-139 has a high level of seed yielding ability which should make it an economically feasible variety to produce for commercial markets. The low susceptibility of Ba 70-139 to rust and lodging under typical seed field conditions should aid in producing economical seed crops. Comparative results on seed yield, rust, and lodging are shown in Table 25 and Table 26.

TABLE 25

Seed Yield Comparisons of Ba 70-139 and Other Bluegrass Varieties in Oregon.

| Variety | Year 1 | Year 2 | Mean |
|---|---|---|---|
| Ba 70-139 | 643 | 930 | 787 |
| Ba 72-492 | 585 | 864 | 725 |
| Ba 72-500 | 559 | 757 | 658 |
| Victa | 780 | 1394 | 1087 |
| Newport | 435 | 1256 | 846 |
| Bristol | 347 | 808 | 578 |
| Mosa | 322 | 1060 | 691 |
| LSD(.05) | 140 | 134 | |

Rating: Pounds per acre of conditioned seed.

TABLE 26

Plant Characteristics of Ba 70-139 and Other Bluegrass Varieties at Gervais, Oregon Under Seed Production Conditions.

| | Rust | Lodging Year 1 | Lodging Year 2 |
|---|---|---|---|
| Ba 70-139 | 2 | 2.5 | 0 |
| Ba 72-500 | 1 | 2.5 | 0.2 |
| Ba 72-492 | 1 | 2.5 | 0.2 |
| Victa | 2 | 2.0 | 0 |
| Bristol | 4 | 4.0 | 1 |
| Newport | 4 | 4.0 | 1 |
| Mosa | 4 | 2.0 | 0 |

Ratings
Rust: 1–4, 4 = very susceptible
Lodging: 0–5, 5 = severe lodging

What is claimed is:

1. A variety of Kentucky bluegrass plant, substantially as shown and described, characterized particularly by a high level of resistance to diseases, a desirable green color throughout the growing season, a high quality persistent turf under a wide range of environmental conditions including shady conditions, and a high level of seed yielding capacity.

* * * * *